US006251852B1

(12) United States Patent
Gould et al.

(10) Patent No.: US 6,251,852 B1
(45) Date of Patent: Jun. 26, 2001

(54) COMBINATION THERAPY FOR REDUCING THE RISKS ASSOCIATED WITH CARDIOVASCULAR DISEASE

(75) Inventors: Robert J. Gould, Green Lane, PA (US); Steven A. Nichtberger, New Rochelle, NY (US); Patricia A. Rhymer, Martinsville, NJ (US); Lars Olofsson, Åkersberga (SE)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/929,595

(22) Filed: Sep. 15, 1997

Related U.S. Application Data

(60) Provisional application No. 60/026,581, filed on Sep. 18, 1996.

(51) Int. Cl.$^7$ .............................. A61K 38/00; C07K 5/00; C07K 7/00
(52) U.S. Cl. .................................. 514/2; 514/17
(58) Field of Search ................. 514/2, 17, 824; 424/184.1

(56) References Cited

U.S. PATENT DOCUMENTS 5,674,893   10/1997   Behounek et al. ................... 514/451

FOREIGN PATENT DOCUMENTS

| 0 671 171 | 9/1995 | (EP) . |
|---|---|---|
| WO 95/13 063 | 5/1995 | (WO) . |

OTHER PUBLICATIONS

Kjekshus et al., *The American Journal of Cardiology*, vol. 76, Sep. 28, 1995, pp 64c–68c.*
Beigel et al., Journal of Internal Medicine, "Lovastatin therapy in heterozygous familial hypercholesterolaemic . . . ", vol. 230, pp. 23–27 (1991).
Alessandri et al., Current Therapeutic Research, "Effects of Hydroxymethylglutaryl–coenzyme a Reductase . . . ", vol. 53(2), pp. 188–195 (1993).
Gerique et al., Atherosclerosis, "Effects of Lovastatin and Filicol (A Microporous Cholestyramine) on . . . ", vol. 115 (Suppl.), p. S105–S105 (1995).
DiMinno et al., Arteriosclerosis, "Increased Fibrinogen Binding to Platelets from Patients with Familial Hypercholesterolemia . . . ", vol. 6, pp. 203–211 (1986).
Cook et al., Drugs of the Future, "Platelet glycoprotein llb/llla antagonists", vol. 19(2), pp. 135–159 (1994).
Cox et al., Medicinal Research Reviews, "The Pharmacology of the Integrins", vol. 14(2), pp. 195–228 (1994).

* cited by examiner

*Primary Examiner*—Avis M. Davenport
(74) *Attorney, Agent, or Firm*—Carol S. Quagliato; Melvin Winokur

(57) ABSTRACT

The instant invention involves a combination therapy and pharmaceutical compositions comprised of a therapeutically effective amount of a cholesterol reducing agent such as an HMG-CoA reductase inhibitor in combination with a platelet aggregation inhibitor which is useful for inhibiting platelet aggregation, for inhibiting the formation of thrombotic occlusions, and for treating, preventing and reducing the risk of occurrence of cardiovascular and cerebrovascular events and related vaso-occlusive disorders.

42 Claims, No Drawings

COMBINATION THERAPY FOR REDUCING THE RISKS ASSOCIATED WITH CARDIOVASCULAR DISEASE

This application claims benefit of Provisional Appl. 60/026,581 filed Sep. 18, 1996.

FIELD OF THE INVENTION

The instant invention involves a combination therapy comprising the administration of a cholesterol reducing agent such as a 3-hydroxy-3-methylglutaryl coenzyme A (HMG-CoA) reductase inhibitor (or HMG-CoA RI) and a platelet aggregation inhibitor for treating, preventing and reducing the risk of developing cardiovascular and cerebrovascular events and disorders in a mammal.

BACKGROUND OF THE INVENTION

Platelet activation and aggregation are involved in unstable angina and acute myocardial infarction, in reocclusion following thrombolytic therapy and angioplasty, in transient ischemic attacks and in a variety of other vasoocclusive disorders. When a blood vessel is damaged either by acute intervention such as angioplasty, or more chronically by the pathophysiological processes of atherosclerosis, platelets are activated to adhere to the disrupted surface and to each other. This activation, adherence and aggregation may lead to occlusive thrombus formation in the lumen of the blood vessel.

Antiplatelet therapy has been used in a wide variety of cardiovascular disease states and in conjunction with interventional therapy such as coronary artery or peripheral bypass grafting, cardiac valve replacement, and percutaneous transluminal coronary angioplasty (PTCA). Available drugs, such as aspirin and ticlopidine (TICLID®), have shown efficacy in syndromes involving vascular occlusion, presumably due to sustained inhibition of platelet function. However, the inhibitory effects of aspirin and ticlopidine are dependent upon the agonist which activates the platelet. For example, aspirin is effective in blocking platelet aggregation induced by agonists such as collagen that are dependent upon the cylooxygenase pathway. It is, however, less effective against concentrations of thrombin which can act by cyclooxygenase independent pathways. Likewise, the inhibitory effects of ticlopidine, which inhibits ADP induced platelet aggregation, can be overcome by combinations of agonists. Thus, an efficacious platelet aggregation therapy that acts independently of the agonist and the pathway activating the platelet could be an important therapeutic advance giving greater efficacy than aspirin or ticlopidine alone in a broader spectrum of thrombotic events.

Integrin Superfamily

The firm attachment of endothelial cells to the subendothelial extracellular matrix is mediated via CAMs, which serve as receptors recognizing an array of adhesive proteins in the extracellular matrix. These proteins include von Willebrand factor (vWf), fibronectin, vitronectin, thrombospondin, laminins, collagen fibrils, elastin, microfibrils of elastin, and glycosaminoglycans. Most of the matrix adhesive molecules are the ligands for integrin receptors expressed in endothelial cells.

Integrins constitute an extended family ("superfamily") of membrane receptors interacting with adhesive proteins in plasma and extracellular matrix and with other membrane receptors (counter-receptors). The name "integrin" implies that they integrate the ligands on the outside of the cell with the cytoskeletal apparatus in the inside of the cell. Integrin receptors consist of a noncovalently linked $Ca^{2+}$-dependent, heterodimeric glycoprotein complex composed of $\alpha$ and $\beta$ subunits. The eight known integrin $\beta$ subunits give rise to eight families in which one "founder" $\beta$ subunit forms heterodimers with different $\alpha$ subunits. There are at least 14 known $\alpha$ subunits. Receptors belonging to the $\beta_1$ and $\beta_3$ families are expressed in endothelial cells. The $\beta_1$ family, also named Very Late Antigens (VLA), is represented by the fibronectin receptor ($\alpha_5\beta_1$, or VLA-5), the collagen receptor ($\alpha_2\beta_1$, or VLA-2) and the laminin receptor ($\alpha_6\beta_1$). The $\beta_3$ family is represented by the vitronectin receptor ($\alpha_v\beta_3$), which is structurally similar (the same $\beta_3$ subunit) to the platelet integrin receptor for fibrinogen, glycoprotein (GP) IIb/IIIa complex (also referred to as $\alpha_{IIb}\beta_3$). The functional difference between these two receptors is that the platelet receptor recognizes the $\gamma$ chain domain (HHLGGAKQAGDV) of human fibrinogen and the endothelial vitronectin receptor does not. Both recognize the sequence R-G-D identified as the cell adhesion site of fibronectin, vitronectin, vWf, and the $\alpha$ chain of human fibrinogen. Therefore, synthetic peptides containing the R-G-D sequence cause detachment of endothelial cells from the extracellular in matrix in vitro.

GP IIb/IIIa Antagonists

The final obligatory step in platelet aggregation is the binding of fibrinogen to an activated membrane-bound glycoprotein complex, GP IIb/IIIa. Platelet activators such as thrombin, collagen, epinephrine or ADP, are generated as an outgrowth of tissue damage. During activation, GP IIb/IIIa undergoes changes in conformation that results in exposure of occult binding sites for fibrinogen. There are six putative recognition sites within fibrinogen for GP IIb/IIIa and thus fibrinogen can potentially act as a hexavalent ligand to crossing GP IIb/IIIa molecules on adjacent platelets. A deficiency in either fibrinogen or GP IIb/IIIa prevents normal platelet aggregation regardless of the agonist used to activate the platelets. Since the binding of fibrinogen to its platelet receptor is an obligatory component of normal aggregation, GP IIb/IIIa is an attractive target for an antithrombotic agent.

Results from clinical trials of GP IIb/IIIa inhibitors support this hypothesis. The monoclonal antibody 7E3, which blocks the GP IIb/IIIa receptor, has been shown to be an effective therapy for the high risk angioplasty population. It is used as an adjunct to percutaneous transluminal coronary angioplasty or atherectomy for the prevention of acute cardiac ischemic complications in patients at high risk for abrupt closure of the treated coronary vessel. Although 7E3 blocks both the IIb/IIIa receptor and the $\alpha_v\beta_3$ receptor, its ability to inhibit platelet aggregation has been attributed to its function as a IIb/IIIa receptor binding inhibitor.

A study reported in The New England Journal of Medicine vol. 330, No. 14, pp. 956–961 (1994) showed a decrease from 12.8% to 8.3% in the combined endpoints of death, non-fatal myocardial infarction (MI) and need for urgent revascularization with fibrinogen receptor blockade. This benefit was at the expense of some additional risk of bleeding, with the need for transfusion increasing from 3% to 6%, and the incidence of patients with decreased hematocrit increasing from 7% to 15%. 7E3 was added to the standard regime of heparin and aspirin thus leaving few hemostatic control mechanisms intact. The clinical benefits of this drug could be seen at 6 months.

Many other studies have shown that blocking the GPIIb/IIIa receptor will stop platelet aggregation induced by all of the agonists and thus prevent thrombus formation but leave platelet adhesion relatively intact. The 7E3 monoclonal antibody is described in Coller et al., *Ann. NY Acad. Sci.* 1991; 614:193–213; and Coller et al., *J. Clin Invest.* 1985; 76:101–108. Others have used agents based on the RGD sequence, including snake venom proteins, small peptides, and peptidomimetics (Cook et al., *Drugs of Future,* 1994; 19:135–159; and Cox et al., *Medicinal Research Reviews,* 1994; 14:195–228).

The snake venom proteins, termed disintegrins, have provided important structural information, but their antigenicity has limited their development as therapeutic agents (Cook et al., ibid.; and Cox et al., ibid.). Integrelin (also known as INTEGRILIN™) is a cyclic peptide that is based on the KGD sequence in the snake venom protein barbourin (Cook et al., ibid.; and Cox et al., ibid.). It inhibits ligand binding to GP IIb/IIIa but has very little effect on ligand binding to $\alpha_v\beta_3$. Among the non-peptide compounds are Ro 44-9883 and MK-383, which are administered intravenously, and are also selective for GPIIb/IIIa (Cook et al., ibid.; and Cox et al., ibid.). Orally active agents include SC54684, which is a prodrug (i.e., it requires biotransformation in vivo to its active form) with high oral bioavailability and Ro 43-8857, GR144053, and DMP728, which are themselves the active inhibitors (Cook et al., ibid.; and Cox et al., ibid.). Literally thousands of other compounds have been synthesized in an attempt to obtain optimal potency, metabolic stability, receptor specificity, and favorable intravascular survival. Despite variations in these compounds, virtually of all of them when they are in their active form retain the basic charge relations of the RGD sequence with a positive charge separated from a negative charge by approximately 10–20 Å (Cook et al., ibid.; and Cox et al., ibid.).

Platelet aggregation is profoundly inhibited when increasing concentrations of murine 7E3 or c7E3 Fab are added to platelet-rich plasma in vitro or administered in incremental doses to animals or humans in vivo (Coller et al., *Ann. NY Acad.,* ibid.; Tcheng et al., ibid.; and Simoons et al., *Circulation* 1994; 89:596–603). There is an excellent correlation between the percentage of receptors blocked and the inhibition of aggregation, with nearly complete inhibition of aggregation when 80% or more of the receptors are blocked (Coller et al., *Ann. NY Acad.,* ibid.).

The results of the 7E3 study support the hypothesis that blockade of GPIIb/IIIa receptors is more effective than aspirin in preventing platelet thrombi, even in the presence of heparin. They also support the hypothesis that platelet-dependent thrombi frequently contribute significantly to the development of ischemic complications after PTCA, even when minor mechanical dissections are present.

It has been clear for several decades that elevated blood cholesterol is a major risk factor for coronary heart disease, and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. With the introduction of lovastatin, the first inhibitor of HMG-CoA reductase to become available for prescription in 1987, for the first time physicians were able to obtain large reductions in plasma cholesterol with very few adverse effects.

Recent studies have unequivocally demonstrated that lovastatin, simvastatin and pravastatin, all members of the HMG-CoA reductase inhibitor class, slow the progression of atherosclerotic lesions in the coronary and carotid arteries. Simvastatin and pravastatin have also been shown to reduce the risk of coronary heart disease events, and in the case of simvastatin a highly significant reduction in the risk of coronary death and total mortality has been shown by the Scandinavian Simvastatin Survival Study. This study also provided some evidence for a reduction in cerebrovascular events. Additional studies have shown that HMG CoA RI's may have an effect on platelet aggregation.

Improved treatments for inhibiting platelet aggregation are currently being sought for the large number of individuals who are at risk for reocclusion following thrombolytic therapy and angioplasty, transient ischemic attacks and a variety of other vaso-occlusive disorders. The instant invention addresses this problem by providing a combination therapy comprised of a platelet aggregation inhibitor with an HMG-CoA RI, and more particularly, a GP IIa/IIIb receptor antagonist with an HMG-CoA RI. When administered as part of a combination therapy, the platelet aggregation inhibitor together with the HMG-CoA RI provide enhanced inhibition of platelet aggregation as compared to administration of either the HMG-CoA RI or the platelet aggregation inhibitor alone. Due to the greater benefit of the drug combination, lesser dosage amounts of the platelet aggregation inhibitor, and more particularly the GP IIa/IIIb receptor antagonist, may be needed to achieve the desired clinical result, thereby resulting in improved safety.

SUMMARY OF THE INVENTION

One object of the instant invention is to provide a novel combination therapy comprised of a therapeutically effective amount of a cholesterol reducing agent such as an HMG-CoA reductase inhibitor in combination with a platelet aggregation inhibitor which is useful for inhibiting platelet aggregation and for inhibiting the formation of thrombotic occlusions in mammals. The instant invention further provides novel methods for treating, preventing and reducing the risk of occurrence of cardiovascular and cerebrovascular events and related vaso-occlusive disorders. Another object of this invention is to provide pharmaceutical compositions which can be used with the above-described methods. A further object is to provide a kit comprised of an HMG-CoA reductase inhibitor composition and a platelet aggregation inhibitor composition. Additional objects will be evident from the following detailed description.

DETAILED DESCRIPTION OF THE INVENTION

The instant invention involves a novel combination therapy comprising the administration of a therapeutically effective amount of an HMG-CoA RI in combination with a therapeutically effective amount of a platelet aggregation inhibitor to a mammal, and more particularly, to a human. The combination therapy is used to inhibit platelet aggregation in mammals who are in need of such inhibition, and to prevent or treat disorders related to platelet aggregation.

The instant invention also provides pharmaceutical compositions comprised of a therapeutically effective amount of an HMG-CoA RI in combination with a therapeutically effective amount of a platelet aggregation inhibitor and a pharmaceutically acceptable carrier. One embodiment of the instant compositions is a single composition adapted for oral administration comprised of a therapeutically effective amount of an HMG-CoA RI in combination with a therapeutically effective amount of a platelet aggregation inhibitor and a pharmaceutically acceptable carrier.

A compound which inhibits HMG-CoA reductase is used in combination with a platelet aggregation inhibitor to practice the instant invention. Examples of HMG-CoA reductase inhibitors that may be used include but are not limited to lovastatin (MEVACOR®; see U.S. Pat. No. 4,231, 938), simvastatin (ZOCOR®; see U.S. Pat. No. 4,444,784), pravastatin (PRAVACHOL®; see U.S. Pat. No. 4,346,227), fluvastatin (LESCOL®; see U.S. Pat. No. 5,354,772), atorvastatin (LIPITOR®; see U.S. Pat. No. 5,273,995) and cerivastatin (also known as rivastatin; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (Feb. 5, 1996). Preferably, the HMG-CoA RI is selected from lovastatin and simvastatin.

The term HMG-CoA reductase inhibitor is intended to include all pharmaceutically acceptable salt, ester and lactone forms of compounds which have HMG-CoA reductase inhibitory activity, and therefore the use of such salts, esters and lactone forms is included within the scope of this invention.

Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33.

A compound which inhibits platelet aggregation is used in combination with an HMG-CoA reductase inhibitor to practice the instant invention. In one embodiment of the instant invention, the compound which inhibits platelet aggregation is an antagonist for the glycoprotein IIb/IIIa fibrinogen receptor. Examples of glycoprotein IIb/IIIa receptor antagonists are described in U.S. Pat. Nos. 5,470,849, 5,463,011, 5,455,243, 5,451,578, 5,446,056, 5,441,952, 5,422,249, 5,416,099, 5,405,854, 5,397,791, 5,393,760, 5,389,631, 5,380,713, 5,374,622, 5,358,956, 5,344,783, 5,340,798, 5,338,723, 5,334,596, 5,321,034, 5,318,899 (e.g. cyclic heptapeptides such as Mpr-(Acetimidyl-Lys)-Gly-Asp-Trp-Phe-Cys-NH$_2$, Mpr-(Acetimidyl-Lys)-Gly-Asp-Trp-Phe-Pen-NH$_2$, Mpr-(Phenylimidyl-Lys)-Gly-Asp-Trp-Phe-Pen-NH$_2$, and Mpr-(Phenylimidyl-Lys)-Gly-Asp-Trp-Phe-Cys-NH$_2$, wherein Mpr is mercapto propionyl), 5,312,923, 5,294,616, 5,292,756, 5,281,585, 5,272,158, 5,264,420, 5,260,307, 5,239,113 (e.g. ethyl 3-[[4-[[4-(aminoiminomethyl)phenyl]amino]-1,4-dioxobutyl]amino]-4-pentynoate), 5,227,490, 5,206,373, 4,703,036 (e.g. N-Methyl-D-phenylalanyl-N-[(1S)-1-formyl-4-guanidinobutyl]-L-prolinamide); European Patent publication No.'s EP 505 868 (e.g., ((1-(2-((4-(aminoiminomethyl)benzoyl)amino)-3-(4-hydroxyphenyl)-1-oxopropyl)-4-piperidinyl)oxy)-(S)-acetic acid), EP 333 356, and EP 656 348; and International Publication No.'s WO 93/11152 (e.g., N-(2-(2-(((3-((aminoiminomethyl)amino)propyl)amino)-carbonyl)-1-piperidnyl)-1-(cyclohexylmethyl)-2-oxoethyl)-(R,S)-glycine), WO 94/18981, WO 94/22820, WO 95/14683, and WO 97/15568, all of which are herein incorporated by reference, and wherein the scope of this invention includes, but is not limited to, the use of each of the specifically disclosed compounds therein. They are described as useful for inhibiting fibrinogen binding and inhibiting clot formation.

In particular, the GP IIb/IIIa receptor antagonist is selected from the following compounds and the pharmaceutically acceptable salts, esters, and solvates (including hydrates) thereof: [3(R)-[2-piperidin-4-yl)ethyl]-2-piperidone-1]acetyl-3(R)-methyl-β-alanine described in U.S. Pat. No. 5,281,585, (see compound 57 in column 67) and referred to herein as Compound A:

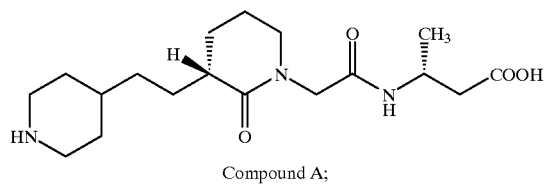

Compound A;

5-[(4-Piperidinyl)methoxy]-2-indolecarbonyl-2(S)-phenylsulfonyl-amino-β-alanine described in WO 97/15568 at page 20 as compound 2-6, and referred to herein as Compound B:

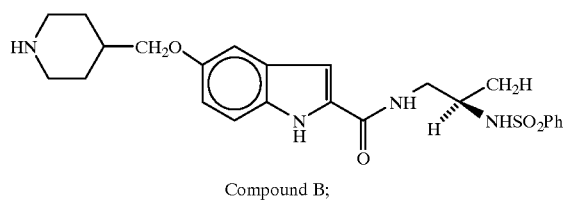

Compound B;

2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid described in WO 94/18981, and referred to herein as Compound C:

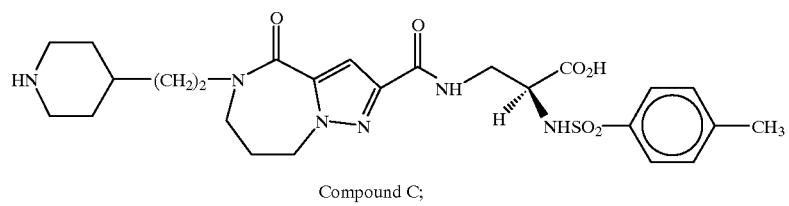

Compound C;

MK-383 (2-S-(n-Butylsulfonylamino)-3 [4-piperidin-4-yl)butyloxyphenyl]propionic acid hydrochloride, and also known as tirofiban) described in U.S. Pat. No. 5,292,756; DMP 728; DMP 754 ((R)-methyl-3-[[[3-[4-(aminoiminomethyl)phenyl]-4,5-dihydro-5-isoxazolyl] acetyl]amino]-N-(butoxycarbonyl)-L-alanine monoacetate) from DuPont-Merck, described in WO 95/14683 and in *Tetrahedron Letters*, 1996, 37 :4455–4458:

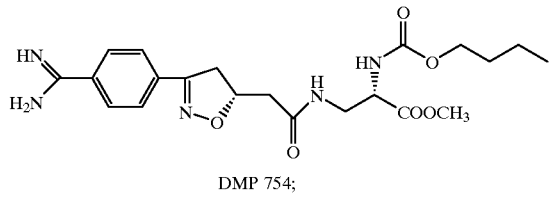

DMP 754;

Ro44-9883, Ro43-8857 and Ro48-3657 (acetic acid, [[1-[2-[[4-[amino(hydroxyimino)methyl]benzoyl]amino]-1-oxopropyl]-4-piperidinyl]oxy]-, ethyl ester, and also known as sibrafiban) from Hoffman-LaRoche; sibrafiban and related compounds are described in EP 656 348:

Sibrafiban;

xemlofiban (ethyl 3-[[4-[[4-(aminoiminomethyl)phenyl] amino]-1,4-dioxobutyl]amino]-4-pentynoate, also known as xemilofiban and SC-54684), particularly the HCl salt thereof, described in U.S. Pat. Nos. 5,344,957 and 5,239,113:

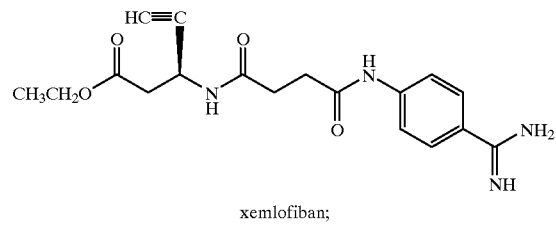

xemlofiban;

fradafiban ((3S,5S)-5-[[(4'-Amidino-4-biphenyl)oxy] methyl]-2-oxo-3-pyrrolidineacetic acid, also known as BIBU-104) as described in U.S. Pat. No. 5,541,343 assigned to Thomae:

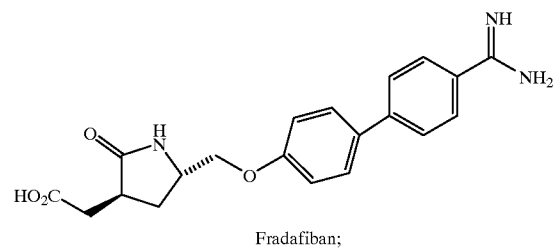

Fradafiban;

orbofiban (N-[[(3S)-1-(p-Amidinophenyl)-2-oxo-3-pyrrolidinyl-carbamoyl]-β-alanine, ethyl ester), particularly the monoacetate and monoacetate hydrate forms thereof, as described in U.S. Pat. No. 5,484,946 assigned to Searle:

Orbofiban;

SB 214857 ((−)-(S)-2-[7-(4,4'-Bipiperidin-1-ylcarbonyl)-4-methyl-3-oxo-2,3,4,5-tetrahydro-1H-1,4-benzodiazepin-2-yl]acetic acid) from SmithKline Beecham, as described in WO 95/18619; ZD-2486 ((R)-3-Methyl-4-[4-[4-(4-pyridyl) piperazin-1-yl]phenoxy]butyric acid) from Zeneca, as described in U.S. Pat. Nos. 5,556,977 and 5,563,141; TAK-029 from Takeda; RPR 109891 from Rhone Polenc Rorer, GR144053 from Glaxo; GR233548 from Glaxo; and SDZ 562 from Sandoz.

The compounds MK-383, DMP 728, Ro44-9883, Ro43-8857, SC-54684 and GR144053 are described in Cook et al., *Drugs of the Future,* 1994, 19(2) :135–159, and Cox et al., *Medicinal Research Reviews,* 1994, 14 :195–228. DMP 728 is also described in *Circulation,* 1996, 93 :537–543; and GR144053 is also described in *Thrombosis and Hematosis,* 1993, 69 :1071. TAK 029 is described in *J. Pharmacology and Experimental Therapeutics,* 1996, 277 :502–510. Xemlofiban is described in *Circulation,* 1995, 92 :2331.

More particularly, the GP IIb/IIIa receptor antagonist is selected from Compound A, Compound B, and DMP 754, which are all orally available compounds. Most particularly, the GP IIb/IIIa receptor antagonist is DMP 754.

One test which is used to evaluate fibrinogen IIb/IIIa receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Compounds which are selective GP IIb/IIIa receptor antagonists may be employed in the instant invention, as well as compounds which block both the GP IIb/IIIa receptor and the $\alpha_v\beta_3$ vitronectin receptor, such as the monoclonal antibody 7E3. Compounds which are selective for the glycoprotein IIb/IIIa receptor are those having a preference (e.g. 10-fold) for binding to IIb/IIIa as compared to other receptors of the integrin family (e.g. $\alpha_v\beta_3$, $\alpha_5\beta_1$, $\alpha_v\beta_5$). Selectivity of these compounds can be readily determined by persons skilled in the art.

In another embodiment of this invention, the compound which inhibits platelet aggregation is one that blocks ADP induced platelet aggregation. Examples of such compounds include ticlopidine (TICLID®), and clopidogrel (PLAVIX®).

In a further embodiment of this invention, the compound which inhibits platelet aggregation is selected from aspirin and dipyridamole.

Herein, the term platelet aggregation inhibitor (or inhibitor of platelet aggregation) is intended to include all pharmaceutically acceptable salt, ester and solvate forms, including hydrates, of compounds which have platelet aggregation inhibitory activity as well as pro-drug forms. Such pro-drugs are compounds which do not have platelet aggregation inhibitory activity outside the body but become active as inhibitors after they are administered to the patient. Therefore the use of such salts, esters solvate forms and pro-drugs of platelet aggregation inhibitors is included within the scope of this invention.

Likewise, the term GP IIb/IIIa receptor antagonist is intended to include all pharmaceutically acceptable salt, ester and solvate forms, including hydrates, of compounds which have GP IIb/IIIa receptor antagonist activity as well as pro-drug forms. Such pro-drugs are compounds which do not have GP IIb/IIIa receptor antagonist activity outside the body but become active as antagonists after they are administered to the patient. Therefore the use of such salts, esters, solvate forms and pro-drugs of GP IIb/IIIa receptor antagonists is also included within the scope of this invention. Pro-drug forms of IIb/IIIa receptor antagonists generally are not active antagonists until after they are metabolised in the body to the active drug form; such prodrugs may be, but are not limited to, ester derivatives. Ester derivatives of the described compounds may act as prodrugs which, when absorbed into the bloodstream of a warm-blooded animal, may cleave in such a manner as to release the drug form and permit the drug to afford improved therapeutic efficacy. An example of such a pro-drug is Ro 48-3657.

Herein, the term "pharmaceutically acceptable salts" shall mean non-toxic salts of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, sodium, stearate, subacetate, succinate, tannate, tartrate, teoclate, tosylate, triethiodide, valerate.

The terms "active agent(s)" and "active drug(s)" are used herein as a way to refer to both the HMG-CoA reductase inhibitors and the platelet aggregation inhibitors which are employed in the instant methods and compositions. Both terms are intended to encompass all salt, ester and pro-drug forms of HMG-CoA reductase inhibitors and platelet aggregation inhibitors, even where the pro-drug form is not active itself but is converted to the active drug form after administration.

As used herein, the term "composition" is intended to encompass a product comprising the specified ingredients, in specified amounts where amounts are specified, as well as any product which results directly or indirectly from combination of the specified ingredients, in the specified amounts where amounts are specified.

As used herein, the term "myocardial infarction" is intended to include both Q-wave and non-Q-wave myocardial infarction, unless otherwise noted.

The instant method involves the administration of an HMG-CoA reductase inhibitor in combination with a platelet aggregation inhibitor. This combination therapy includes administration of a single pharmaceutical dosage formulation which contains both the HMG-CoA reductase inhibitor and the platelet aggregation inhibitor, as well as administration of each active agent in its own separate pharmaceutical dosage formulation. While the HMG-CoA reductase inhibitor can be administered orally or parenterally, oral dosing is preferred. The GP IIb/IIIa receptor antagonist can be administered orally, intravenously, transdermally (for example using an iontophoretic patch), intraocularly, intranasally or by other routes known to those skilled in the medical arts, taking into account that certain GP IIb/IIIa receptor antagonists are developed for oral administration while others may be developed for non-oral routes such as intravenous administration. Ticlopidine, clopidogrel, aspirin and dipyridamole are administered orally. Preferably, both active agents of the instant combination therapy are administered orally, and most preferably the active agents are combined in a single oral dosage formulation.

For example, a GP IIb/IIIa receptor antagonist and an HMG-CoA reductase inhibitor can be administered to the patient together in one oral composition such as a tablet or capsule. Another example would be a single oral composition comprised of aspirin and an HMG-CoA reductase inhibitor. Alternatively, the combination therapy may comprise administration of an oral HMG-CoA reductase inhibitor composition with a separate oral aspirin composition, or with a separate GP IIb/IIIa receptor antagonist composition formulated for oral, intravenous, transdermal, intraocular, or intranasal administration.

Where separate dosage formulations are used, the HMG-CoA reductase inhibitor and the platelet aggregation inhibitor can be administered at essentially the same time, i.e., concurrently, or at separately staggered times, i.e, sequentially. Similarly, a GP IIb/IIIa receptor antagonist may be administered on an intravenous regimen, while the patient is orally dosed once a day with a conventional or controlled-release formulation of an HMG-CoA reductase inhibitor. Combination therapy is understood to include all these regimens. Administration in these various ways are suitable for the present invention as long as the beneficial pharmaceutical effect of the platelet aggregation inhibitor and HMG-CoA reductase inhibitor are realized by the patient at substantially the same time. Such beneficial effect is achieved when the target blood level concentrations of each active drug are maintained at substantially the same time. Concurrent oral administration is preferred.

It is expected that a combination therapy of intravenously administered GP IIb/IIIa receptor antagonist with orally administered HMG-CoA reductase inhibitor could be used in response to an acute medical event where inhibition of platelet aggregation is needed, and may generally be administered for a period of time of one or two weeks or up to a month or longer if deemed necessary. Where the combination therapy involves for example oral administration of both the GP IIb/IIIa receptor antagonist and the HMG-CoA reductase inhibitor, the therapy may be administered on a longer-term chronic basis, such as a period of several months or years, for as long as deemed medically appropriate for the patient.

Therapeutically effective amounts of the platelet aggregation inhibitors and the HMG-CoA reductase inhibitors are suitable for use in the compositions and methods of the present invention. The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The dosage regimen utilizing an HMG-CoA RI in combination with a platelet aggregation inhibitor is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the enhanced effects achieved by combining them together must also be taken into account. A consideration of these factors is well within the purview of the ordinarily skilled clinician for the purpose of determining the therapeutically effective amounts of the drug combination needed to prevent, counter, or arrest the progress of the condition.

Dosage information for HMG-CoA RI's is well known in the art, since several HMG-CoA RI's are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50$^{th}$ Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA RI is from about 1 to 200 mg/day, and more preferably from about 5 to 160 mg/day. However, dosage amounts will vary depending on the potency of the specific HMG-CoA reductase inhibitor used as well as other factors as noted above. Also, the dosage amount of HMG-CoA reductase inhibitor needed to achieve the desired effect will be affected by the dosage amount and potency of the IIb/IIIa receptor antagonist or other platelet aggregation inhibitor which is employed in the combined therapy. An HMG-CoA RI which has sufficiently greater potency may be given in sub-milligram daily dosages.

As examples, the daily dosage amount for simvastatin may be selected from 5 mg, 10 mg, 20 mg, 40 mg, 80 mg and 160 mg; for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg, and more particularly from 5 mg to 80 mg, including dosage amounts of 10 mg, 20 mg and 40 mg. Oral administration may be in single or divided doses of two, three, or four times daily, although a single daily dose of the HMG-CoA RI is preferred.

Oral dosages of GP IIb/IIIa receptor antagonists when used for the indicated effects, will range between about 0.001 mg per kg of body weight per day (mg/kg/day) to about 50 mg/kg/day and preferably 0.005–20 mg/kg/day and most preferably 0.005–10 mg/kg/day. Suitable oral tablets and capsules contain between 0.1 mg and 5 g, preferably between 0.5 mg and 2 g, most preferably between 0.5 mg and 1 g, for example, 0.5 mg, 1 mg, 5 mg, 10 mg, 50 mg, 150 mg, 250 mg, or 500 mg of GP IIb/IIIa receptor antagonist. Oral administration may be in one or divided doses of two, three, or four times daily. A single daily dose is preferred.

Intravenously, the most preferred doses for GP IIb/IIIa receptor antagonists will range from about 0.5 pg to about 5 mg/kg/minute during a constant rate infusion, to achieve a plasma level concentration during the period of time of administration of between 0.1 ng/ml and 1 $\mu$g/ml.

Dosage amounts for ticlopidine are described in the *Physicians' Desk Reference*. Dosage amounts of aspirin for the indicated effects are known to those skilled in medical arts, and generally range from about 75 mg to about 325 mg per day. For example, a formulation may contain 75 mg, 80 mg, 160 mg, 250 mg, or 325 mg of aspirin.

Suitable oral formulations of clopidogrel may contain from 25 mg to 500 mg, preferably from 75 mg to 375 mg, and most preferably from 75 mg to 150 mg of clopidogrel. For example, the formulation may contain 25 mg, 50 mg, 75 mg, 150 mg, 250 mg, or 500 mg of clopidogrel. Oral administration may be in one or divided doses of two, three, or four times daily. A single daily dose is preferred.

The active agents employed in the instant combination therapy can be administered in such oral forms as tablets, capsules (each of which includes sustained release or timed release formulations), pills, powders, granules, elixirs, tinctures, suspensions, syrups, and emulsions. The instant invention includes the use of both oral rapid-release and time-controlled release pharmaceutical formulations (see, e.g., U.S. Pat. No. 5,366,738 which describes controlled release formulations). Suitable intravenous compositions for the GP IIb/IIIa receptor antagonists include bolus or extended infusion. Such oral and intravenous compositions are known to those of ordinary skill in the pharmaceutical arts. For example, see *Remington's Pharmaceutical Sciences,* Mack Publishing Co., Easton, Pa.

The active drugs can be administered in admixture with pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants (BHA, BHT, propyl gallate, sodium ascorbate, citric acid) can also be added to stabilize the dosage forms. Other suitable components include gelatin, sweeteners, natural and synthetic gums such as acacia, tragacanth or alginates, carboxymethylcellulose, polyethylene glycol, waxes and the like.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

The compositions and methods of the present invention may be used as treatment for acute cardiovascular and cerebrovascular events, as well as for chronic therapy for prevention or reduction of risk of occurrence of cardiovascular and cerebrovascular events. For example, the compositions of this invention, and methods for administering the combination therapy of a platelet aggregation inhibitor with an HMG-CoA reductase inhibitor, are useful for treating, preventing or reducing the risk of occurrence of acute coronary ischemic syndrome in mammals, and more particularly in humans, who are at risk of developing acute coronary ischemic syndrome. Acute coronary ischemic syndrome includes the conditions of unstable angina and non-Q-wave myocardial infarction.

Compositions and methods of the invention may be used to prevent or reduce the risk of formation of thrombi and thromboemboli and therefore to prevent or reduce the risk of thrombotic occlusions and reocclusions. They are useful in surgery on peripheral arteries (arterial grafts, carotid endaterectomy) and in cardiovascular surgery where manipulation of arteries and organs, and/or the interaction of platelets with artificial surfaces, leads to platelet aggregation and potential formation of thrombi and thromboemboli. For example, the combination therapy can be used for preventing or reducing the risk of occurrence of platelet thrombosis, thromboembolism and reocclusion after acute intervention such as atherectomy, angioplasty (PTCA), coronary artery bypass procedures or cardiac valve replacement. The combination therapy can also be used for preventing or reducing the risk of occurrence of platelet thrombosis, thromboembolism and reocclusion during and after thrombolytic therapy. Since blood vessels can also sustain chronic damage by the pathophysiological processes of atherosclerosis, patients with atherosclerosis can also be treated with the instant combination therapy to prevent or reduce the risk of occlusive thrombus formation. The instant combination therapy can be used to treat, prevent or reduce the risk of intermittent claudication, which is a clinical manifestation of peripheral vessel disease. Combination therapy of an HMG-CoA reductase inhibitor with a GP IIb/IIIa receptor antagonist may reduce the risk of thrombocytopenia.

The instant combination therapy can also be used to treat, prevent or reduce the risk of a first or subsequent Q-wave myocardial infarction in persons at risk for such events as well as to prevent or reduce the risk of restenosis in persons at risk for restenosis. Additionally, the instant combination therapy can be used for treating, preventing or reducing the risk of occurrence of acute cerebrovascular ischemic events such as a first or subsequent thrombotic stroke or transient ischemic attack. In general, the instant combination therapy can be used whenever antiplatelet therapy, or inhibition of platelet aggregation, is needed.

The compositions and methods of the present invention are also useful in combination with procedures for treating patients with other anticoagulants (e.g. thrombin inhibitors such as heparin and Factor Xa inhibitors such as warfarin), and thrombolytic agents (e.g. streptokinase and tissue plasminogen activator). The instant combination therapy can also be co-adminstered with a β-adrenergic receptor blocker. In particular, a combination of an HMG-CoA RI with aspirin can be co-administered with a β-adrenergic receptor blocker to reduce the risk of coronary heart disease and cerebrovascular clinical events such as myocardial infarction, stroke and cardiovascular death, particularly in post-MI patients. Examples of β-adrenergic receptor blockers include but are not limited to acebutolol, atenolol, betaxolol, bioprolol, carteolol, labetalol, metoprolol, nadolol, penbutolol, pindolol, propanolol, and timolol. Dosage amounts of β-adrenergic receptor blockers are described in the PDR.

In accordance with this invention, a therapeutically effective amount of an HMG-CoA RI and a therapeutically effective amount of a platelet aggregation inhibitor can be used for the preparation of a medicament useful for inhibiting platelet aggregation, and for treating, preventing or reducing the risk of developing acute coronary ischemic syndrome in mammals, particularly in humans. Additionally, a therapeutically effective amount of an HMG-CoA RI and a therapeutically effective amount of a platelet aggregation inhibitor can be used for the preparation of a medicament useful for preventing or reducing the risk of formation of thrombi and thromboemboli, for preventing or reducing the risk of thrombotic occlusions and reocclusions, for treating, preventing or reducing the risk of a first or subsequent myocardial infarction, for preventing or reducing the risk of restenosis, for treating, preventing or reducing the risk of acute cerebrovascular ischemic events such as a first or subsequent thrombotic stroke or transient ischemic attack, and for halting or slowing the progression of atherosclerotic disease. More particularly, a therapeutically effective amount of an HMG-CoA RI and a therapeutically effective amount of a platelet aggregation inhibitor can be used together for the preparation of a medicament suitable for oral administration which is useful for the above-described treatments. Similarly, a therapeutically effective amount of an HMG-CoA RI can be used for the preparation of a medicament for use in combination with a therapeutically effective amount of a platelet aggregation inhibitor, which is useful for the above-described treatments. Also, a therapeutically effective amount of a platelet aggregation inhibitor can be used for the preparation of a medicament for use in combination with a therapeutically effective amount of an HMG-CoA RI, which is useful for the above-described treatments.

An additional embodiment of the instant invention involves a kit comprised of an HMG-CoA RI in an oral dosage formulation and a platelet aggregation inhibitor in a separate oral dosage formulation. More particularly, the kit is comprised of an HMG-CoA RI selected from the group consisting of lovastatin, simvastatin, pravastatin, fluvastatin, atorvastatin and cerivastatin; and the platelet aggregation inhibitor is selected from the group consisting of a GP IIb/IIIa receptor antagonist, ticlopidine, clopidogrel, aspirin and dipyridamole. In one class of this embodiment the HMG-CoA RI is selected from lovastatin and simvastatin, and more particularly the HMG-CoA RI is simvastatin. In a second class of this embodiment, the platelet aggregation inhibitor is a GP IIb/IIIa receptor antagonist selected from the group consisting of Compound A, Compound B, and DMP 754. In a third class of this embodiment, the platelet aggregation inhibitor is aspirin.

One example of this embodiment is a kit comprised of an oral dosage formulation of simvastatin and an oral dosage formulation of aspirin. The packaging for the kit could be designed and manufactured in a variety of ways. A preferred example is a blister package containing rows of a simvastatin tablet and an aspirin tablet placed side by side on the same blister card, each of the two tablets in its own blister bubble, with calendar or similar type markings on the card that convey to the user that one "pair" of tablets (i.e., one simvastatin tablet and one aspirin tablet) is to be ingested per day. A kit containing simvastatin and a GP IIb/IIIa receptor antagonist such as Compound A, Compound B, or DMP 754 could be designed in a similar fashion.

A further class of this embodiment involves the kit described above further comprising an oral dosage formulation of a pharmaceutically active agent selected from a β-adrenergic receptor blocker and an angiotensin II receptor antagonist, in addition to the HMG-CoA RI and the platelet aggregation inhibitor. More particularly, β-adrenergic receptor blockers without intrinsic sympathomimetic activity (ISA) and without alpha blocking properties have a cardioprotective effect for patients who have had a myocardial infarction and can be employed in the kit. Atenolol, metoprolol, betaxolol and acebutolol are beta blockers without ISA. Losartan potassium is currently marketed in the U.S. under the trademark COZAAR®, and is one example of an angiotensin II receptor antagonist that could be employed in the kit. Dosages for beta blockers and for losartan potassium are commonly known to those skilled in the pharmaceutical arts and can be found, for example in the *Physician's Desk Reference*.

Examples of dosage formulations are as follows.

EXAMPLE 1

Tablet Preparation

Tablets containing simvastatin and a glycoprotein IIb/IIIa receptor antagonist can be prepared as illustrated below:

| Ingredient | Amount |
|---|---|
| simcastatin | 1 mg – 222 mg. |
| glycoprotein IIb/IIIa receptor antagonist | 0.1 mg – 5 g |
| diluent, binder, disintegrant, lubricant (excipients) | qs. 200 – 400 mg. |

EXAMPLE 2

Tablet Preparation

Tablet containing 25.0, 50.0 and 100.0 mg, repectively, of a GP IIb/IIIa receptor antagonist are prepared as illustrated below:
TABLE FOR DOSES CONTAINING FROM 25–100 MG OF GP IIB/IIIA RECEPTOR ANTAGONIST

| | Amount - mg | | |
|---|---|---|---|
| GP IIb/IIIa receptor antagonist | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 3

Intravenous formulations
An intravenous dosage form of the GP IIb/IIIa receptor antagonist is prepared as follows:

| | Amount |
|---|---|
| GP IIb/IIIa receptor antagonist | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for treating a cardiovascular event selected from acute coronary ischemic syndrome and Q-wave myocardial infarction comprising acute administration of a therapeutically effective amount of an HMG-CoA reductase inhibitor in combination with a therapeutically effective amount of a platelet aggregation inhibitor to a mammal in need of such treatment.

2. A method for treating a cerebrovascular event selected from thrombotic stroke and transient ischemic attack comprising administration of a therapeutically effective amount of an HMG-CoA reductase inhibitor in combination with a therapeutically effective amount of a platelet aggregation inhibitor to a mammal in need of such treatment.

3. The method of claim 2 wherein the platelet aggregation inhibitor is selected from the group consisting of a glycoprotein IIb/IIIa receptor antagonist, ticlopidine, clopidogrel, aspirin and dipyridamole.

4. The method of claim 2 wherein the platelet aggregation inhibitor is a glycoprotein IIb/IIIa receptor antagonist.

5. The method of claim 4 wherein the platelet aggregation inhibitor is selected from the group consisting of:

(a) [3(R)-[2-piperidin-4-yl)ethyl]-2-piperidone-1]acetyl-3(R)-methyl-β-alanine;
(b) 5-[(4-piperidinyl)methoxy]-2-indolecarbonyl-2(S)-phenylsulfonyl-amino-β-alanine;
(c) 2(S)-[(p-toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid;
(d) tirofiban;
(e) DMP 728;
(f) DMP 754;
(g) Ro44-9883;
(h) Ro43-8857;
(i) sibrafiban;
(j) xemlofiban;
(k) fradafiban;
(l) orbofiban;
(m) SB 214857;
(n) ZD-2486;
(o) TAK-029;
(p) RPR 109891;
(q) GR144053;
(r) GR233548;
(s) SDZ 562;
(t) Mpr-(Har)-Gly-Asp-Trp-Phe-Cys-$NH_2$;

and the pharmaceutically acceptable salts, esters, pro-drugs and solvates thereof.

6. The method of claim 4 wherein the platelet aggregation inhibitor is selected from DMP 728; Ro44-9883; Ro43-8857; SB 214857; ZD-2486; TAK-029; RPR 109891; GR144053; GR233548; SDZ 562 and the pharmaceutically acceptable salts, esters, pro-drugs and solvates thereof.

7. The method of claim 4 wherein the platelet aggregation inhibitor is selected from tirofiban, DMP 754, fradafiban, Mpr-(Har)-Gly-Asp-Trp-Phe-Cys-$NH_2$ and the pharmaceutically acceptable salts, esters, pro-drugs and solvates thereof.

8. The method of claim 4 wherein the platelet aggregation inhibitor is selected from tirofiban and the pharmaceutically acceptable salts, esters, pro-drugs and solvates thereof.

9. The method of claim 4 wherein the platelet aggregation inhibitor is selected from DMP 754 and the pharmaceutically acceptable salts, esters, pro-drugs and solvates thereof.

10. The method of claim 2 wherein the HMG-CoA reductase inhibitor is selected from the group consisting of pravastatin, fluvastatin, atorvastatin and cerivastatin and the pharmaceutically acceptable salt, ester and lactone forms thereof.

11. The method of claim 2 wherein the HMG-CoA reductase inhibitor is selected from lovastatin and the pharmaceutically acceptable salt and ester forms thereof.

12. The method of claim 2 wherein the HMG-CoA reductase inhibitor is selected from simvastatin and the pharmaceutically acceptable salt and ester forms thereof.

13. The method of claim 3 wherein the HMG-CoA reductase inhibitor is selected from simvastatin and the pharmaceutically acceptable salt and ester forms thereof.

14. The method of claim 4 wherein the HMG-CoA reductase inhibitor is selected from simvastatin and the pharmaceutically acceptable salt and ester forms thereof.

15. The method of claim 5 wherein the HMG-CoA reductase inhibitor is selected from simvastatin and the pharmaceutically acceptable salt and ester forms thereof.

16. The method of claim 6 wherein the HMG-CoA reductase inhibitor is selected from simvastatin and the pharmaceutically acceptable salt and ester forms thereof.

17. The method of claim 7 wherein the HMG-CoA reductase inhibitor is selected from simvastatin and the pharmaceutically acceptable salt and ester forms thereof.

18. The method of claim 8 wherein the HMG-CoA reductase inhibitor is selected from simvastatin and the pharmaceutically acceptable salt and ester forms thereof.

19. The method of claim 9 wherein the HMG-CoA reductase inhibitor is selected from simvastatin and the pharmaceutically acceptable salt and ester forms thereof.

20. The method of claim 1 wherein the drug combination is administered for up to 30 days following the cardiovascular event.

21. The method of claim 1 wherein the cardiovascular event is acute coronary ischemic syndrome.

22. The method of claim 1 wherein the cardiovascular event is Q-wave myocardial infarction.

23. The method of claim 1 wherein the a platelet aggregation inhibitor is selected from the group consisting of a glycoprotein IIb/IIIa receptor antagonist, ticlopidine, clopidogrel, aspirin and dipyridamole.

24. The method of claim 1 wherein the platelet aggregation inhibitor is a glycoprotein IIb/IIIa receptor antagonist.

25. The method of claim 24 wherein the platelet aggregation inhibitor is selected from the group consisting of:
(a) [3(R)-[2-piperidin-4-yl)ethyl]-2-piperidone-1]acetyl-3(R)-methyl-β-alanine;
(b) 5-[(4-piperidinyl)methoxy]-2-indolecarbonyl-2(S)-phenylsulfonyl-amino-β-alanine;
(c) 2(S)-[(p-toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid;
(d) tirofiban;
(e) DMP 728;
(f) DMP 754;
(g) Ro44-9883;
(h) Ro43-8857;
(i) sibrafiban;
(j) xemlofiban;
(k) fradafiban;
(l) orbofiban;
(m) SB 214857;
(n) ZD-2486;
(o) TAK-029;
(p) RPR 109891;
(q) GR144053;
(r) GR233548;
(s) SDZ 562;
(t) Mpr-(Har)-Gly-Asp-Trp-Phe-Cys-$NH_2$;
and the pharmaceutically acceptable salts, esters, pro-drugs and solvates thereof.

26. The method of claim 24 wherein the platelet aggregation inhibitor is selected from DMP 728; Ro44-9883; Ro43-8857; SB 214857; ZD-2486; TAK-029; RPR 109891; GR144053; GR233548; SDZ 562 and the pharmaceutically acceptable salts, esters, pro-drugs and solvates thereof.

27. The method of claim 24 wherein the platelet aggregation inhibitor is selected from tirofiban, DMP 754, fradafiban, Mpr-(Har)-Gly-Asp-Trp-Phe-Cys-$NH_2$ and the pharmaceutically acceptable salts, esters, pro-drugs and solvates thereof.

28. The method of claim 24 wherein the platelet aggregation inhibitor is selected from tirofiban and the pharmaceutically acceptable salts, esters, pro-drugs and solvates thereof.

29. The method of claim 24 wherein the platelet aggregation inhibitor is selected from DMP 754 and the pharmaceutically acceptable salts, esters, pro-drugs and solvates thereof.

30. The method of claim 1 wherein the HMG-CoA reductase inhibitor is selected from the group consisting of pravastatin, fluvastatin, atorvastatin and cerivastatin and the pharmaceutically acceptable salt, ester and lactone forms thereof.

31. The method of claim 1 wherein the HMG-CoA reductase inhibitor is selected from lovastatin and the pharmaceutically acceptable salt and ester forms thereof.

32. The method of claim 1 wherein the HMG-CoA reductase inhibitor is selected from simvastatin and the pharmaceutically acceptable salt and ester forms thereof.

33. The method of claim 20 wherein the HMG-CoA reductase inhibitor is selected from simvastatin and the pharmaceutically acceptable salt and ester forms thereof.

34. The method of claim 21 wherein the HMG-CoA reductase inhibitor is selected from simvastatin and the pharmaceutically acceptable salt and ester forms thereof.

35. The method of claim 22 wherein the HMG-CoA reductase inhibitor is selected from simvastatin and the pharmaceutically acceptable salt and ester forms thereof.

36. The method of claim 23 wherein the HMG-CoA reductase inhibitor is selected from simvastatin and the pharmaceutically acceptable salt and ester forms thereof.

37. The method of claim 24 wherein the HMG-CoA reductase inhibitor is selected from simvastatin and the pharmaceutically acceptable salt and ester forms thereof.

38. The method of claim 25 wherein the HMG-CoA reductase inhibitor is selected from simvastatin and the pharmaceutically acceptable salt and ester forms thereof.

39. The method of claim 26 wherein the HMG-CoA reductase inhibitor is selected from simvastatin and the pharmaceutically acceptable salt and ester forms thereof.

40. The method of claim 27 wherein the HMG-CoA reductase inhibitor is selected from simvastatin and the pharmaceutically acceptable salt and ester forms thereof.

41. The method of claim 28 wherein the HMG-CoA reductase inhibitor is selected from simvastatin and the pharmaceutically acceptable salt and ester forms thereof.

42. The method of claim 29 wherein the HMG-CoA reductase inhibitor is selected from simvastatin and the pharmaceutically acceptable salt and ester forms thereof.

* * * * *